United States Patent [19]

Schinkel et al.

[11] 4,236,072
[45] Nov. 25, 1980

[54] ADJUSTING MECHANISM

[75] Inventors: Willem Schinkel; Cornelis Versluijs, both of Almelo, Netherlands

[73] Assignee: U.S. Philips Corporation, New York, N.Y.

[21] Appl. No.: 18,494

[22] Filed: Mar. 8, 1979

[30] Foreign Application Priority Data

Mar. 21, 1978 [NL] Netherlands .......................... 7803026

[51] Int. Cl.³ ....................... G01N 23/20; G21K 1/00; G21K 7/00
[52] U.S. Cl. ............................... 250/277 CH; 250/278
[58] Field of Search ........... 250/272, 273, 274, 277 R, 250/277 CH, 278, 279, 280; 350/21, 22, 23

[56] References Cited

U.S. PATENT DOCUMENTS 3,566,111  2/1971  Harm .................................... 250/278

Primary Examiner—Alfred E. Smith
Assistant Examiner—Thomas P. O'Hare
Attorney, Agent, or Firm—T. A. Briody; R. T. Mayer; P. R. Miller

[57] ABSTRACT

A mechanism is provided for varying the distance between a detector and a measuring crystal in an X-ray spectrometer. The crystal is arranged on a rotatable shaft and the detector is arranged on an arm which can perform a circular movement about the crystal shaft. The crystal shaft and the detector arm are coupled so that a rotation of the crystal shaft through an angle $\theta$ is accompanied by a rotation of the detector arm through an angle $2\theta$. A first pulley having a radius r is mounted on the crystal shaft and a second disc having a radius 2r is rotatably mounted on the crystal shaft. A belt or cord is guided over each one of two guide rollers. One end of each of these belts is permanently connected to the first pulley, while its other end is permanently connected to the second pulley.

3 Claims, 2 Drawing Figures

ADJUSTING MECHANISM

The invention relates to a mechanism for varying the distance between a detector and a measuring crystal, notably suitable for use in an X-ray spectrometer, the crystal being arranged on a rotatable shaft and the detector being arranged on an arm which is capable of performing a circular movement around the crystal shaft, the crystal shaft and the detector arm being coupled so that a rotation of the crystal shaft through an angle $\theta$ is accompanied by a rotation of the detector arm through an angle $2\theta$.

A mechanism of the described kind is known from U.S. Pat. No. 3,566,111. These mechanisms are used, for example, in X-ray spectrometers, the principal elements of which are formed by a specimen holder, a measuring crystal and a detector. The X-radiation emerging from an X-ray tube is projected from the specimen onto the crystal at a given angle, after which it is reflected to the detector at the same angle. During operation, the crystal is rotated through a given angle; and in order to ensure that the reflected radiation is always incident of the detector, the detector should perform a rotation through twice the angle at the same time.

It is an object of the invention to provide a mechanism for the movements of the crystal and the detector which has a simpler and more compact construction than the known mechanism. The invention also has for its object to provide a mechanism of the described kind enabling easy adjustment of the positions of the crystal and the detector relative to each other.

In order to achieve these objects, the mechanism in accordance with the invention is characterized in that on the crystal shaft there is arranged a first pulley having a radius r, a second pulley having a radius 2r being rotatably journalled on the crystal shaft, the mechanism furthermore comprising two guide rollers, over each of which a belt or cord is guided, one end of each of the belts being permanently connected to the first pulley while its other end is permanently connected to the second pulley.

The two pulleys are thus interconnected in a play-free manner, rotation of the crystal shaft through a given angle thus causing the second pulley, together with the detector arm connected thereto, to rotate through twice the angle. The play-free coupling has a very simple and compact construction.

In order to enable adjustment of the crystal and the detector with respect to each other, the guide rollers in a further preferred embodiment are rotatably journalled in a bearing block which is tiltable about an axis which is situated in the plane through the crystal shaft, perpendicularly to the plane through both shafts of the guide rollers.

By simultaneous displacement of the two guide rollers, one in the direction of the crystal shaft and one in the direction away therefrom, the crystal can be rotated without displacement of the detector.

The driving of the crystal shaft can be realized, for example, by means of an electric step motor, which drives a worm which cooperates with a worm wheel on the crystal shaft. The number of steps performed by the motor is then used as a measure for the angular rotation of the crystal shaft. Because a given play is present between worm and worm wheel, this method of measuring the angular rotation of the crystal shaft is not particularly accurate. Notably in a mechanism in accordance with the invention, in which the play in the transmission between crystal shaft and detector arm is reduced to zero, it is important to detect the position of the crystal shaft also as accurately as possible. In order to realize this object, a further preferred embodiment of the mechanism in accordance with the invention is characterized in that a belt or cord is guided around a further pulley which is rigidly mounted on the crystal shaft, said belt or cord being permanently connected to this pulley and being guided over a guide wheel and being coupled to a measuring head or a ruler which cooperates with a stationary ruler or measuring head, respectively.

The angular rotation of the crystal shaft is thus converted without play into a translation of the measuring head or the ruler coupled to the belt or cord, it being possible to measure such displacement by means of the ruler or measuring head, respectively, with the displacement being a measure for the angular rotation of the shaft.

The invention will be described in detail hereinafter with reference to the accompanying diagrammatic drawing.

Figure 1:
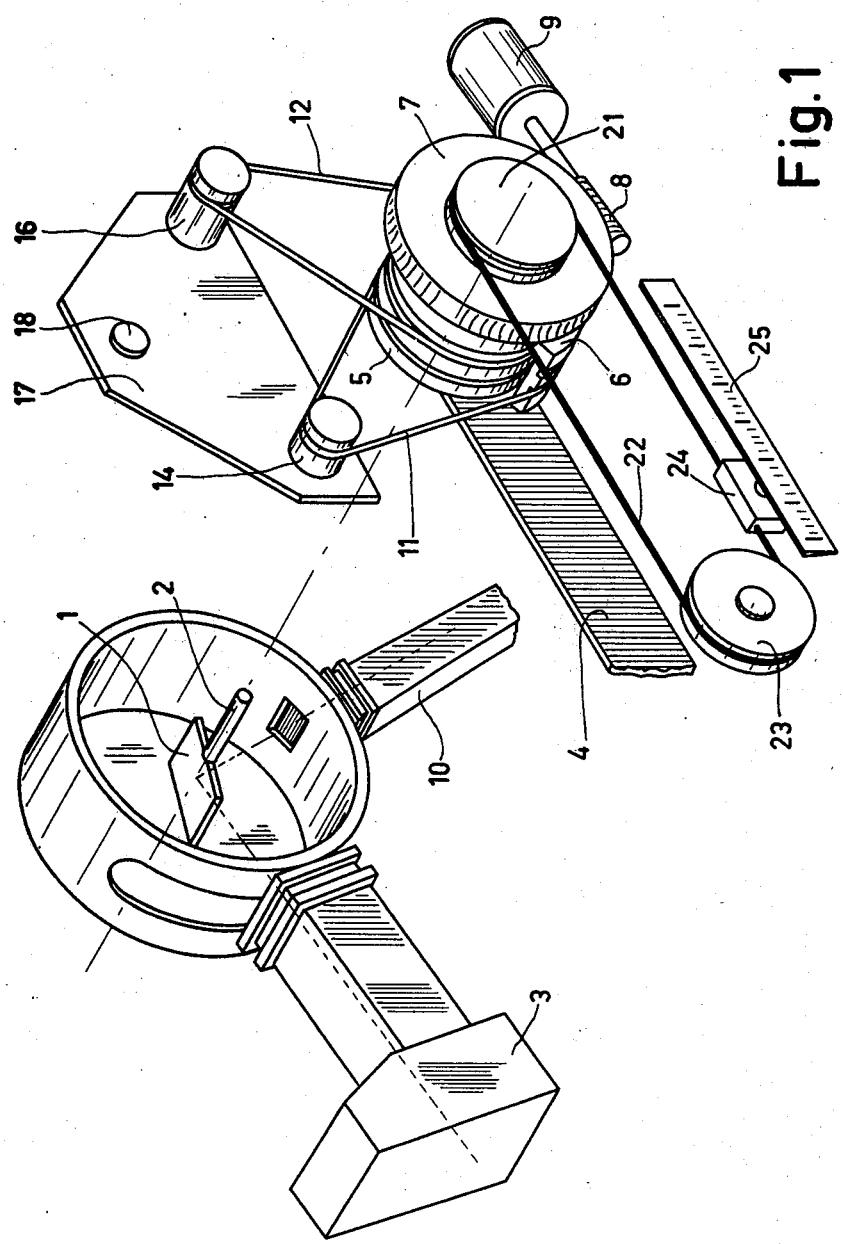
FIG. 1 is a perspective exploded view of a part of an X-ray spectrometer.
Figure 2:
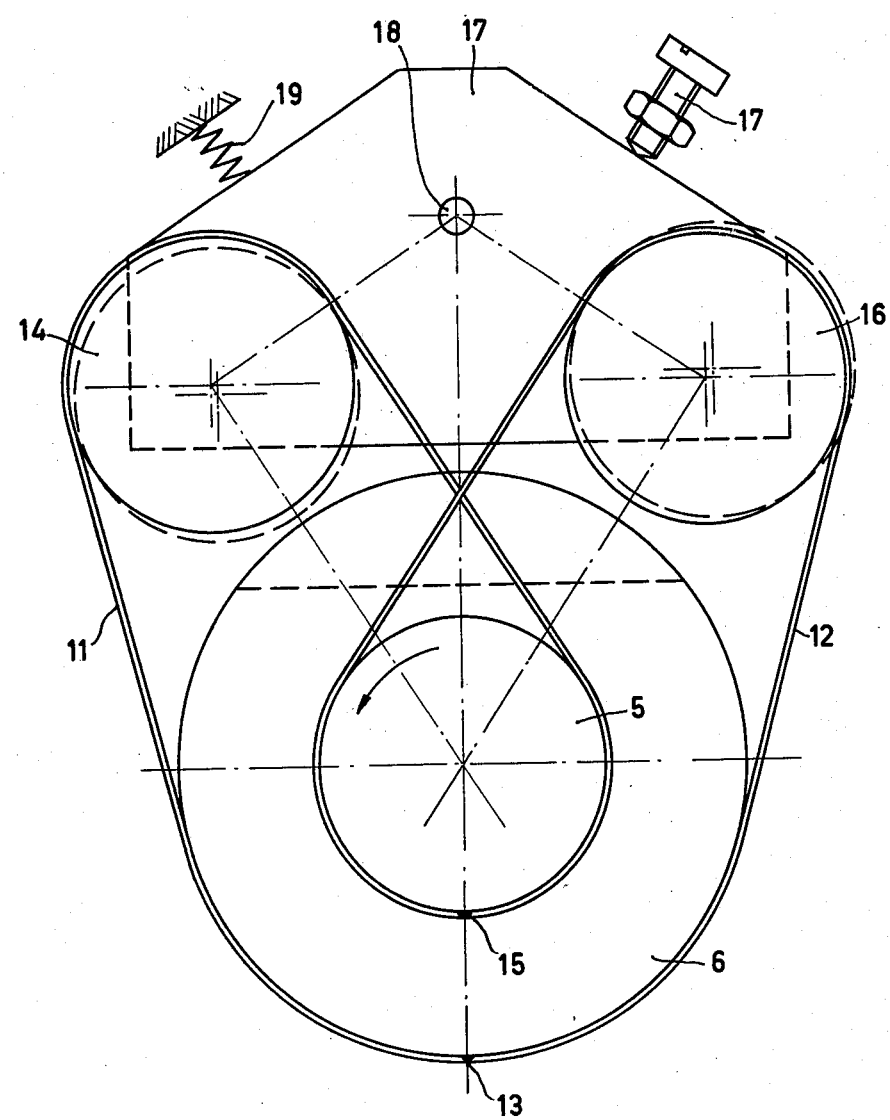
FIG. 2 is a front view of the transmission mechanism of FIG. 1.

The reference numeral 1 in FIG. 1 denotes a crystal which is mounted on a rotatable shaft 2. The reference numeral 3 denotes a detector which is mounted on a lever 4. At its side which is remote from the detector 3, the lever 4 is connected to a pulley 5, which is rotatably journalled on the shaft 2. A pulley 6 is rigidly mounted on the shaft 2. The shaft 2 furthermore supports a worm wheel which cooperates with a worm 8 which is coupled to an electric motor 9. The X-ray source (not shown) emits X-rays which are incident, through the entrance duct 10, on the crystal 2 by way of a specimen. These rays are deflected to the detector 3 from the crystal 1. During the measuring process, the crystal 1 is rotated through a given angle. In order to ensure that the reflected X-rays continue to be incident on the detector 3, the detector 3 must be rotated in the same direction as the crystal but through twice the angle. In order to achieve this, the pulleys 5 and 6 of the detector arm 4 and the crystal shaft 2, respectively, are coupled to each other by belts or cords 11 and 12. At the area 13 in FIG. 2, the belt 11 is rigidly connected to the pulley 6, is guided over a roller 14, and its other end is rigidly connected to the pulley 5 at the area 15. Also at the area 13, the belt 12 is rigidly connected to the pulley 6, is guided over a second guide roller 16, and its other end is rigidly coupled to the pulley 5 at the area 15. The pulley 5 has a radius r and the pulley 6 has a radius 2r. During rotation of the shaft 2 through an angle $\theta$ by way of the motor 9, the worm 8 and the worm wheel 7, the pulley 6 will also rotate through an angle $\theta$ because it is rigidly mounted on the shaft 2.

This implies a given displacement of the point 13 over a distance $2r \times \theta$. Because the point 13 is rigidly connected to the point 15 on the pulley 5 via belts 11 and 12, the point 15 will also be displaced over the same distance $2r \times \theta$. However, because the radius of the pulley 5 is only r, the pulley 5 will have to rotate through an angle $2\theta$. The desired rotation ratio of crystal and detector is thus obtained.

In order to enable adjustment of the pulleys 5 and 6 with respect to each other, the guide rollers 14 and 16

(see FIG. 2) are rotatably journalled in a bearing block 17 which can be tilted about a pivot 18. On the one side, the bearing block 17 is subject to a pressure spring 19, and on its other side, an adjusting screw 20 presses against the block. The adjusting screw 20 can be used to tilt the bearing block 17 slightly about the point 18. As a result of this operation, for example, the guide roller 16 is slightly lifted and the guide roller 14 is slightly lowered which, when the detector pulley 5 is held, results in a displacement of the point 13 to the right in FIG. 2, and hence in a rotation of the crystal pulley 6.

A very simple, play-free coupling between crystal and detector is thus realized and also the possibility of adjustment of the crystal and also the possibility of adjustment of the crystal and the detector with respect to each other.

A pulley 21 is also rigidly mounted on the shaft 2. Over this pulley a belt 22 is guided which is rigidly connected to the pulley. The belt 22 is furthermore guided over a guide wheel 23. The belt 22 supports a measuring head 24 which cooperates with a graduated ruler 25. The angular rotation of the shaft 2 is thus converted without pay into a translation of the measuring head 24, it being possible to measure said translation accurately in known manner by means of the ruler.

Instead of connecting the measuring head to the belt and arranging the ruler to be stationary, it is alternatively possible to couple the ruler to the belt and to arrange the measuring head, to be stationary.

What is claimed is:

1. A mechanism for varying distance between a detector and measuring crystal in an X-ray spectrometer comprising:
    a crystal mounted on a rotatable shaft,
    a detector arranged on an arm moving about said shaft,
    a first pulley mounted on said rotatable shaft and having a radius r,
    a second pulley rotatably journaled on said rotatable shaft and having a radius 2r,
    at least a pair of guide rollers, and
    driving means for moving said detector through an angle $2\theta$ when said rotatable shaft is moved through an angle $\theta$, said driving means comprising at least two belts guided respectively over each of said guide rollers and each having one end attached to said first pulley and a second end attached to said second pulley.

2. A mechanism according to claim 1, wherein said guide rollers are rotatably journaled in a bearing block, said bearing block being tiltable about an axis located in a plane perpendicular to said rotatable shaft, said axis extending parallel to axes of rotation of said guide rollers.

3. A mechanism according to claims 1 or 2, wherein a further pulley is rigidly mounted on said rotatable shaft and a further belt connected to said further pulley and passing over a guide wheel, said further belt being coupled to one of a measuring head or ruler cooperating with one of a stationary ruler or measuring head.

* * * * *